United States Patent
Hochrein

(10) Patent No.: US 9,791,263 B2
(45) Date of Patent: Oct. 17, 2017

(54) MEASURING DEVICE FOR REFLECTION MEASUREMENTS OF TEST OBJECTS AND METHOD FOR MEASURING RADIATION REFLECTED BY TEST OBJECTS

(71) Applicant: INOEX GmbH, Melle (DE)

(72) Inventor: Thomas Hochrein, Würzburg (DE)

(73) Assignee: INOEX GmbH, Melle (DE)

( * ) Notice: Subject to any disclaimer, the term of this patent is extended or adjusted under 35 U.S.C. 154(b) by 0 days.

(21) Appl. No.: 15/055,391

(22) Filed: Feb. 26, 2016

(65) Prior Publication Data

US 2016/0238375 A1 Aug. 18, 2016

Related U.S. Application Data

(63) Continuation of application No. PCT/DE2014/100304, filed on Aug. 26, 2014.

(30) Foreign Application Priority Data

Aug. 27, 2013 (DE) .......... 10 2013 217 038

(51) Int. Cl.
*G01B 11/06* (2006.01)
*G01N 29/04* (2006.01)
(Continued)

(52) U.S. Cl.
CPC ......... *G01B 11/06* (2013.01); *G01N 21/3581* (2013.01); *G01N 21/55* (2013.01);
(Continued)

(58) Field of Classification Search
CPC .......... G01N 21/4788; G01N 21/3581; G01N 21/55; G01N 29/04; G01N 29/221; G01J 3/0237; G01J 5/0205; G01B 11/06
See application file for complete search history.

(56) References Cited

U.S. PATENT DOCUMENTS 9,201,052 B2 * 12/2015 Ho ............ G01N 21/3581
2004/0095147 A1 5/2004 Cole
(Continued)

FOREIGN PATENT DOCUMENTS

EP 0 453 946 A2 10/1991
EP 1 980 817 A2 10/2008
(Continued)

OTHER PUBLICATIONS

German Office Action, dated Jul. 27, 2014, in German Application No. 10 2013 217 038.6 filed Aug. 27, 2013 (7 pages).
(Continued)

*Primary Examiner* — David Porta
*Assistant Examiner* — Faye Boosalis
(74) *Attorney, Agent, or Firm* — Shlesinger, Arkwright & Garvey LLP

(57) ABSTRACT

A measuring device for reflection measurements of test objects includes a transmitter for emitting radiation, a first collimation element for aligning the emitted radiation, a first focusing element for focusing emitted radiation in relation to the test object, and a receiver for detecting radiation reflected by the test object. There is a second collimation element for aligning the reflected radiation, and a second focusing element for focusing the reflected radiation in relation to the receiver. At least two of the first and second collimation elements and first and second focusing elements are separate from each other. Thus, a simple and flexible design of the measuring device is achieved, which can be adapted to the test object.

20 Claims, 5 Drawing Sheets

(51) Int. Cl.
*G01N 21/3581* (2014.01)
*G01N 21/55* (2014.01)
*G01N 29/22* (2006.01)

(52) U.S. Cl.
CPC ........... *G01N 29/04* (2013.01); *G01N 29/221* (2013.01); *G01N 2291/02854* (2013.01)

(56) References Cited

U.S. PATENT DOCUMENTS

2009/0290149 A1* 11/2009 Roth ................. G01N 21/3581
356/300
2012/0217403 A1* 8/2012 Sartorius ............ G01N 21/3581
250/339.12

FOREIGN PATENT DOCUMENTS

| GB | 2 405 263 A | 2/2005 |
|---|---|---|
| GB | 2 446 026 A | 7/2008 |
| WO | WO 2011/098943 A1 | 8/2011 |

OTHER PUBLICATIONS

International Search Report (SR) and Written Opinion in PCT/DE2014/10034, dated Dec. 5, 2014 (15 pages).

* cited by examiner ular 0.05 THz to 20 THz, and
MEASURING DEVICE FOR REFLECTION MEASUREMENTS OF TEST OBJECTS AND METHOD FOR MEASURING RADIATION REFLECTED BY TEST OBJECTS

CROSS-REFERENCE TO RELATED APPLICATIONS

This application is a continuation of Application No. PCT/DE2014/100304, filed 26 Aug. 2014, which claims the priority of German Patent Application No. 10 2013 217 038.6, filed 27 Aug. 2013, and each of which is incorporated herein by reference.

FIELD OF THE INVENTION

The present invention relates to a measuring device for reflection measurements of test objects, and method for measuring radiation reflected on test objects.

The invention relates to a measuring device for reflection measurements of test objects according to the preamble of Claim 1. The invention further relates to a method for measuring radiation reflected on test objects. The radiation used for the measurement is in particular terahertz radiation.

BACKGROUND OF THE INVENTION

Reflection measurements of test objects are carried out, for example, to determine the wall thickness of the test objects. Compared to transmission measurements, reflection measurements have the advantage that the test object has to be accessible only on one side. However, a disadvantage of reflection measurements is the small signal-to-noise ratio, since for measurements of test objects made of plastics, for example, the reflectance is lower than the transmittance.

To obtain the highest possible signal quality of the measured radiation, the receiver is separate from the transmitter. For example, a measuring device for reflection measuring measurements is known from US 2004/095147 A1, in which a dielectric body is situated between a terahertz transmitter and the test object, and between the test object and a terahertz receiver, to improve the signal quality. A disadvantage of the known measuring device is that it has a less flexible and complicated design.

OBJECTS AND SUMMARY OF THE INVENTION

The object of the invention, therefore, is to provide a measuring device for reflection measurements of test objects, which has a simple, flexible design and is adaptable to the test object.

This object is achieved by a measuring device having the features of Claim 1. As a result of at least two of the elements from the group which comprise the first collimation element, the first focusing element, the second collimation element, and the second focusing element being separate from one another, the measuring device may have a simple, flexible design and may be adapted to the test object or to the available installation space. Individual elements may be easily changed, depending on the test object, so that the signal quality and/or the required installation space may be optimized. The transmitter and the receiver are separate, so that the receiver is optimally adaptable to the reflected radiation and an optimal signal quality of the measured radiation achieved. The emitted radiation and/or reflected radiation have/has in particular a frequency in the range of 0.01 THz to 50 THz, in particular 0.05 THz to 20 THz, and in particular 0.1 THz to 5 THz.

A measuring device according to Claim 2 allows a comparatively compact design. As a result of the transmitter and the receiver being situated in succession or one behind the other along the beam direction, i.e., along an optical axis, the transmitter and the receiver may be situated in an overlapping manner. A compact design is achieved in this way. In particular, the first collimation element and the second focusing element are also separate from one another. The first collimation element and the second focusing element may thus be situated in an offset manner along the beam direction and/or designed with different focal lengths.

A measuring device according to Claim 3 ensures a compact design. As a result of the transmitter and the receiver having an overlap area along the beam direction, i.e., being situated in succession and in an overlapping manner along the beam direction, the dimensions transverse to the beam direction may be minimized.

A measuring device according to Claim 4 allows simple manufacture and a flexible design. As a result of the first collimation element and the second focusing element being separate from one another, they may be easily selected, or manufactured according to demand. In particular, their arrangement independent of one another may be adapted to the arrangement and/or design of the transmitter and/or receiver and of a test object holder.

A measuring device according to Claim 5 ensures, in a simple manner, the arrangement of the first collimation element and the second focusing element as a function of the arrangement of the transmitter and/or receiver and/or of a test object holder.

A measuring device according to Claim 6 allows, in a simple manner, an alignment or parallel alignment of the emitted radiation and/or focusing of the reflected radiation. The lens in question preferably has a convex, in particular biconvex or plano-convex, design.

A measuring device according to Claim 7 ensures high signal quality. Signal losses or reflection losses are avoided due to the design of the first collimation element and/or of the second focusing element as a mirror. In addition, mirrors allow a space-saving design of the measuring device which is adaptable to the given installation space. Alignment, in particular parallel alignment, of the emitted radiation and/or focusing of the reflected radiation are/is made possible by the parabolic design. Furthermore, mirrors allow deflection of the radiation.

A measuring device according to Claim 8 allows an arrangement of the first focusing element and/or of the second collimation element independent of the arrangement of the first collimation element and of the second focusing element. An optimal adaptation to the test object and the available installation space is thus possible.

A measuring device according to Claim 9 ensures a simple design. Since the first focusing element and the second collimation element are situated upstream from the test object and downstream from the test object, respectively, in the beam path, they may be easily designed as one part. A simple, accurate arrangement or adjustment is also made possible in this way.

A measuring device according to Claim 10 allows, in a simple manner, focusing of the emitted radiation on the test object and/alignment or parallel alignment of the radiation reflected from the test object. The first focusing element and/or the second collimation element are/is preferably designed as a convex lens. The lens in question in particular has a biconvex or plano-convex design. The first focusing element and the second collimation element preferably have a one-part design.

A measuring device according to Claim 11 allows, in a simple manner, focusing of the emitted radiation on the test object and/or alignment or parallel alignment of the radiation reflected from the test object. The first focusing element and the second collimation element are preferably designed as a parabolic mirror. The first focusing element and the second collimation element preferably have a one-part design. Reflection losses are avoided in this way, thus ensuring high signal quality. In addition, the mirror or mirrors allow(s) deflection of the radiation.

A measuring device according to Claim 12 allows an adaptation of the design to the available installation space. The deflection element is in particular designed as a mirror. A loss-free deflection of the emitted and/or the reflected radiation is thus made possible. The deflection element is preferably situated between the test object or a test object holder and the first focusing element and/or the second collimation element.

A measuring device according to Claim 13 allows a simple, flexible adaptation of the design to the test object. As a result of the first focusing element and/or the second collimation element being displaceable relative to a test object holder and/or the first collimation element and/or the second focusing element, the design is easily adaptable to test objects having different shapes and/or sizes.

A measuring device according to Claim 14 ensures a simple design. The gas or the air in particular has an index of refraction that is less than the index of refraction of the first collimation element and/or of the first focusing element and/or of the second collimation element and/or of the second focusing element. In particular, a gas, in particular air, is situated in the beam path between the first focusing element and a test object holder and between the test object holder and the second collimation element.

A further object of the invention is to provide a method for measuring radiation reflected on test objects, which allows a reflection measurement that is simple and flexible and adapted to the test object.

This object is achieved by a method having the features of Claim 15. The advantages of the method according to the invention correspond to the advantages of the measuring device according to the invention already described. The method may in particular also be further embodied using the features of Claims 2 to 14. The method according to the invention is used in particular for determining a wall thickness of the test object. The test object is in particular made of a plastic material. The emitted radiation and/or the reflected radiation have/has in particular a frequency in the range of 0.01 THz to 50 THz, in particular 0.05 THz to 20 THz, and in particular 0.1 THz to 5 THz.

BRIEF DESCRIPTION OF THE DRAWINGS

Further features, advantages, and particulars of the invention result from the following description of several embodiments.

The figures show the following.

DETAILED DESCRIPTION OF THE INVENTION

Figure 1:
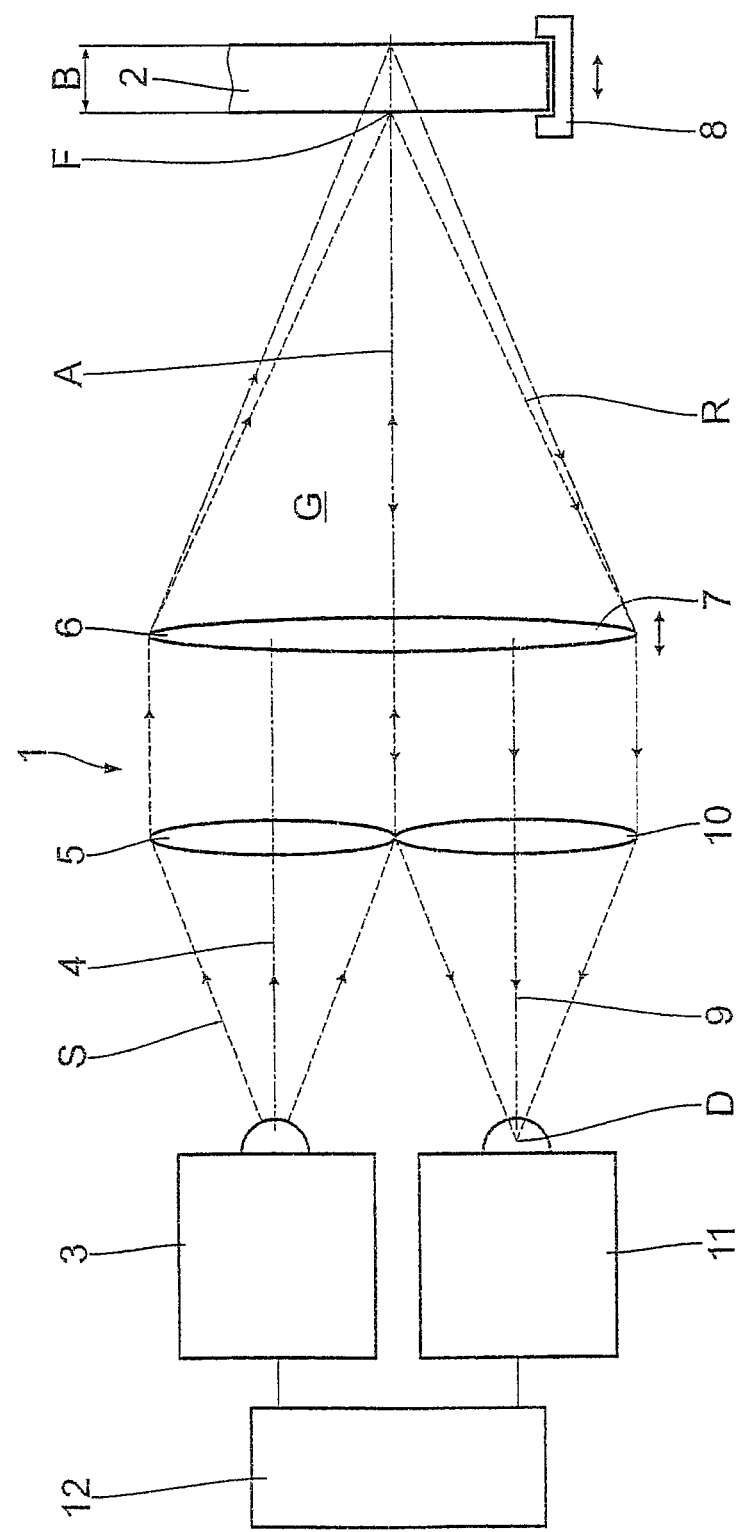
FIG. 1 shows a schematic illustration of a measuring device for reflection measurements of test objects, with lenses for aligning and focusing the emitted and reflected radiation, according to a first embodiment.

A first embodiment of the invention is described below with reference to FIG. 1. A measuring device 1 is used for carrying out reflection measurements of a test object 2. For this purpose, the measuring device 1 has a transmitter 3 which emits radiation having a frequency in the range of 0.01 THz to 50 THz, in particular 0.05 THz to 20 THz, and in particular 0.1 THz to 5 THz. The transmitter 3 or the transmitting antenna has a customary design, and emits the radiation in a cone shape in a beam direction 4. The emitted radiation is denoted by reference character S in FIG. 1. The beam direction 4 defines an optical axis of the transmitter 3.

A first collimation element 5 is situated downstream from the transmitter 3 in the beam direction 4. The first collimation element 5 is designed as a convex lens. The convex lens 5 is situated concentrically with respect to the optical axis of the transmitter 3 or of the radiation cone of the emitted radiation S. The first collimation element 5 is used for the alignment or the parallel alignment of the emitted radiation S.

A first focusing element 6 is situated downstream from the first collimation element 5 in the beam direction 4. The first focusing element 6 is designed as one part with a second collimation element 7. The first focusing element 6 and the second collimation element 7 are designed as a convex lens which is situated concentrically with respect to an optical axis A of the measuring device 1. The emitted radiation S is focused on a focal point F on a surface of the test object 2 by means of the first focusing element 6, i.e., a first half of the convex lens. For this purpose, the test object 2 is held by means of a test object holder 8 which is displaceable relative to the first focusing element 6 and the second collimation element 7 along the optical axis A.

The second collimation element 7, i.e., a second half of the convex lens, is situated downstream from the test object 2 in a reflection direction 9. The reflection direction 9 extends opposite to the beam direction 4. The reflected radiation is denoted below by reference character R. The second collimation element 7 is used for the alignment or the parallel alignment of the reflected radiation R. A second focusing element 10, which focuses the reflected radiation R on a receiver 11, is situated downstream from the second collimation element in the reflection direction 9. The reflection direction 9 defines an optical axis of the receiver 11 or the receiving antenna. The second focusing element 10 is designed as a convex lens which is situated concentrically with respect to the optical axis of the receiver 11. For detecting the reflected radiation R, the second focusing element 10 focuses the reflected radiation R on a focal point D of the receiver 11. The receiver 11 is used for detecting the radiation R reflected on the test object 2. The reflected radiation R has a frequency in the range of 0.01 THz to 50 THz, in particular 0.05 THz to 20 THz, and in particular 0.1 THz to 5 THz.

The transmitter 3 and the receiver 11 as well as the elements 5 and 10, and 6 and 7, are situated symmetrically relative to the optical axis A. The transmitter 3 and the first collimation element 5, as well as the receiver 11 and the second focusing element 10, are aligned with one another, and in particular are not offset with respect to one another, along the beam direction 4 and the reflection direction 9, respectively.

The first collimation element 5 and the second focusing element 10 are separate from one another, and are separate from the first focusing element 6 and the second collimation element 7, respectively. In this way, the elements 5, 10 and 6, 7 may be situated in a simple and flexible manner relative to the transmitter 3 and/or the receiver 11 and/or the test object holder 8. The first focusing element 6 and/or the second collimation element 7 are/is preferably displaceable relative to the first collimation element 5 and/or the second focusing element 10.

The space between the transmitter 3 and the first collimation element 5, and/or the space between the first collimation element 5 and the first focusing element 6, and/or the space between the first focusing element 6 and the test object holder 8 or the test object 2, and/or the space between the test object holder 8 or the test object 2 and the second collimation element 7, and/or the space between the second collimation element 7 and the second focusing element 10, and/or the space between the second focusing element 10 and the receiver 11 is/are filled with a gas G, preferably with air. A simple, flexible design is ensured in this way. In particular, the space between the first focusing element 6, the test object holder 8, and the second collimation element 7 is filled with the gas G or with air.

The transmitter 3 and the receiver 11 are connected to a control apparatus 12 which controls the transmitter 3 and evaluates the reflected and detected radiation R.

The mode of operation of the measuring device 1 is as follows:

The transmitter 3 emits the radiation S with a frequency in the terahertz range. The radiation S is emitted in a cone shape. The first collimation element 5 aligns the emitted radiation S in parallel to the optical axis A. The radiation S aligned in parallel is subsequently focused on the focal point F by the first focusing element 6. The focal point F is situated in particular on the surface of the test object 2. For this purpose, the test object 2 is appropriately positioned by means of the displaceable test object holder 8.

The radiation P reflected on the test object 2 in turn is aligned in parallel to the optical axis A by means of the second collimation element 7. The reflected radiation R aligned in parallel is subsequently focused on the focal point D of the receiver 11 by means of the second focusing element 10. The radiation R detected by the receiver 11 is evaluated by means of the control apparatus 12.

The transmitter 3 or the transmitting antenna and the receiver 11 or the receiving antenna are aligned in parallel, but with an offset with respect to the optical axis A. The emitted radiation S is collimated centrally with respect to the optical axis 4 of the transmitter 3 by the first lens 5, and is focused on the surface of the test object 2 by means of the lens 6 or 7, which is situated centrally with respect to the optical axis A. The test object 2 is situated in the focal point F of the lens 6 or 7. The radiation R reflected in the area of the focal point F is once again collimated by the lens 6 or 7 and focused on the receiver 11 by means of the lens 10. The surface of the test object 2 is preferably aligned vertically in the focal point F so that the largest possible amount of reflected radiation R is reflected in the direction of the receiver 11.

The test object 2 is in particular designed as a plastic component, for example as a plastic pipe. Due to the radiation S being reflected on a front surface and on a rear surface of the test object 2, a wall thickness B of the test object 2 may be determined from the reflected radiation R.

The design of the measuring device 1 is comparatively compact, and may be flexibly adapted to the available installation space. The reflection losses at the interfaces of the collimation elements 5 and 7 and of the focusing elements 6 and 10 are low, as the result of which a comparatively good signal-to-noise ratio is achieved. In particular, due to the separate design of the transmitter 3 and the receiver 11, the reflected radiation R may be evaluated in an optimal manner.

Figure 2:
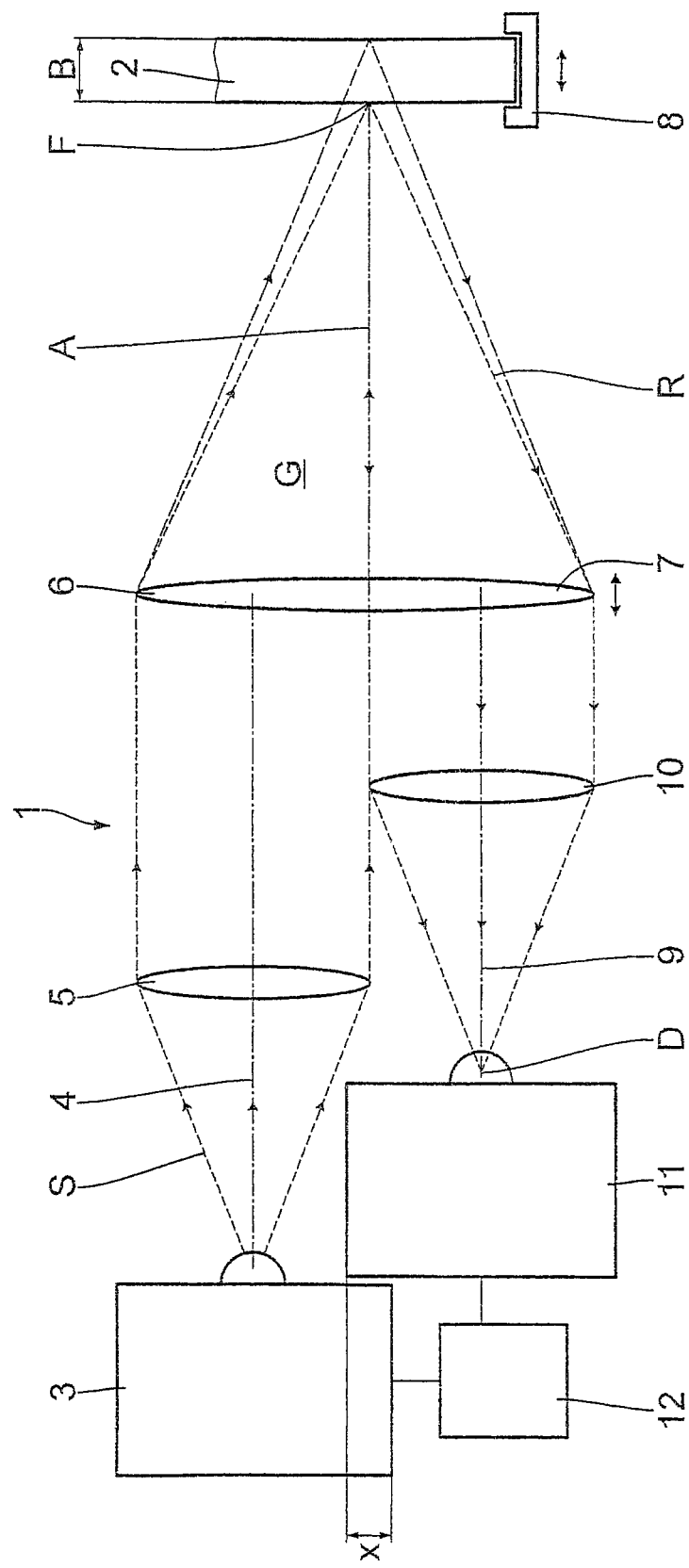
FIG. 2 shows a schematic illustration of a measuring device with a transmitter and receiver situated in an overlapping manner, according to a second embodiment.

A second embodiment of the invention is described below with reference to FIG. 2. In contrast to the first embodiment, the transmitter 3 and the first collimation element 5 are offset with respect to the receiver 11 and the second focusing element 10 along the beam direction 4 or the optical axis A. In addition, the transmitter 3 and the receiver 11 are situated in an overlapping manner, and have an overlap area x. Optimization or the installation space transversely with respect to the optical axis A or the beam direction 4 is thus achieved. With regard to the further design and the mode of operation of the measuring device 1, reference is made to the preceding embodiment.

Figure 3:
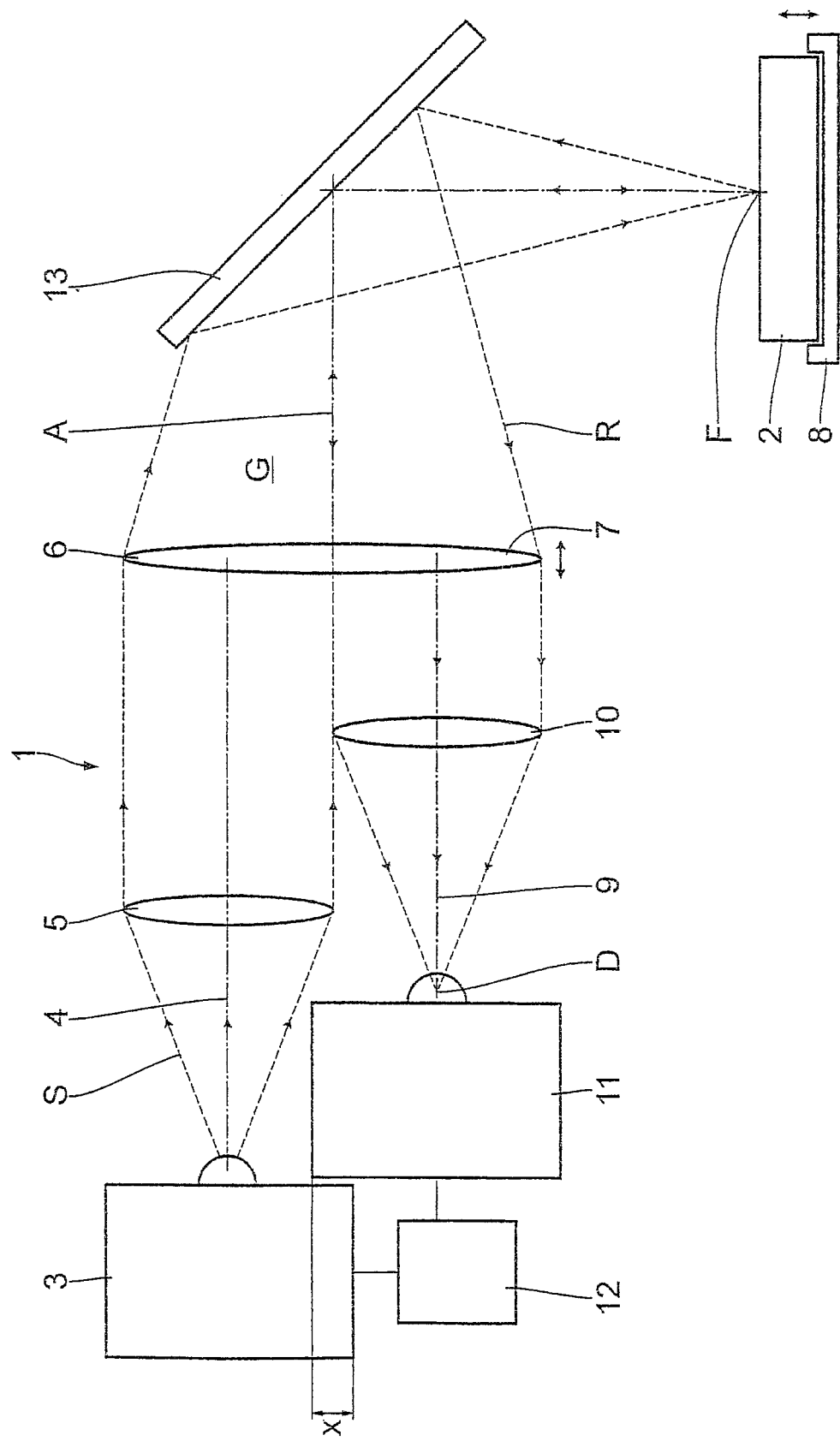
FIG. 3 shows a schematic illustration of a measuring device with a deflection element, according to a third embodiment.

A third embodiment of the invention is described below with reference to FIG. 3. In contrast to the preceding embodiments, the measuring device 1 has a deflection element 13 situated in the beam path between the first focusing element 6 and the test object 2 or the test object holder 8, and between the test object 2 or the test object holder 8 and the second collimation element 7. The space between the first focusing element 6 or the second collimation element 7 and the deflection element 13, and between the deflection element 13 and the test object holder 8, is filled with a gas G, in particular with air, corresponding to the preceding embodiments. The deflection element 13 is designed as a mirror which in particular is planar. An arrangement of the test object 2 at a distance from or transversely with respect to the optical axis A is made possible by the deflection element 13. The measuring device 1 is thus easily and flexibly adaptable to the test object 2 or a given installation space. With regard to the further design and the mode of operation of the measuring device 1, reference is made to the preceding embodiments.

Figure 4:
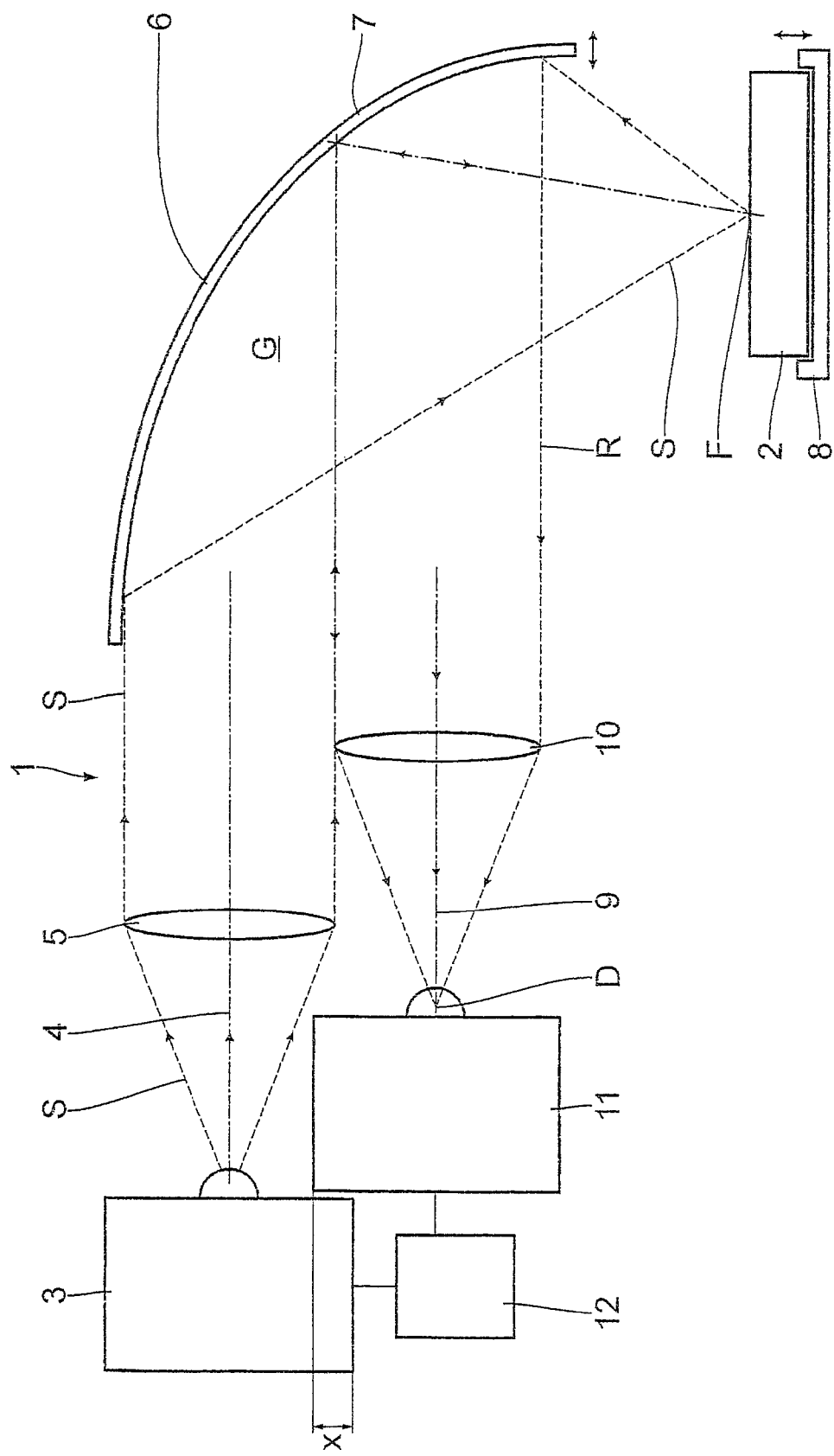
FIG. 4 shows a schematic illustration of a measuring device with a mirror for focusing the emitted radiation and for aligning the reflected radiation, according to a fourth embodiment.

A fourth embodiment of the invention is described below with reference to FIG. 4. In contrast to the preceding embodiments, the first focusing element 6 and the second collimation element 7 are designed in one piece as a mirror. The mirror has a parabolic shape, so that the emitted radiation S is focused and the reflected radiation R is collimated. In addition, the mirror 6 or 7 also deflects the emitted radiation S or the reflected radiation R, respectively, and consequently acts as a deflection element. The space between the mirror 6 or 7 and the test object 2 or the test object holder 8 is filled with a gas G, in particular with air, corresponding to the preceding embodiments. With regard to the further design and the mode of operation of the measuring device 1, reference is made to the preceding embodiments.

Figure 5:
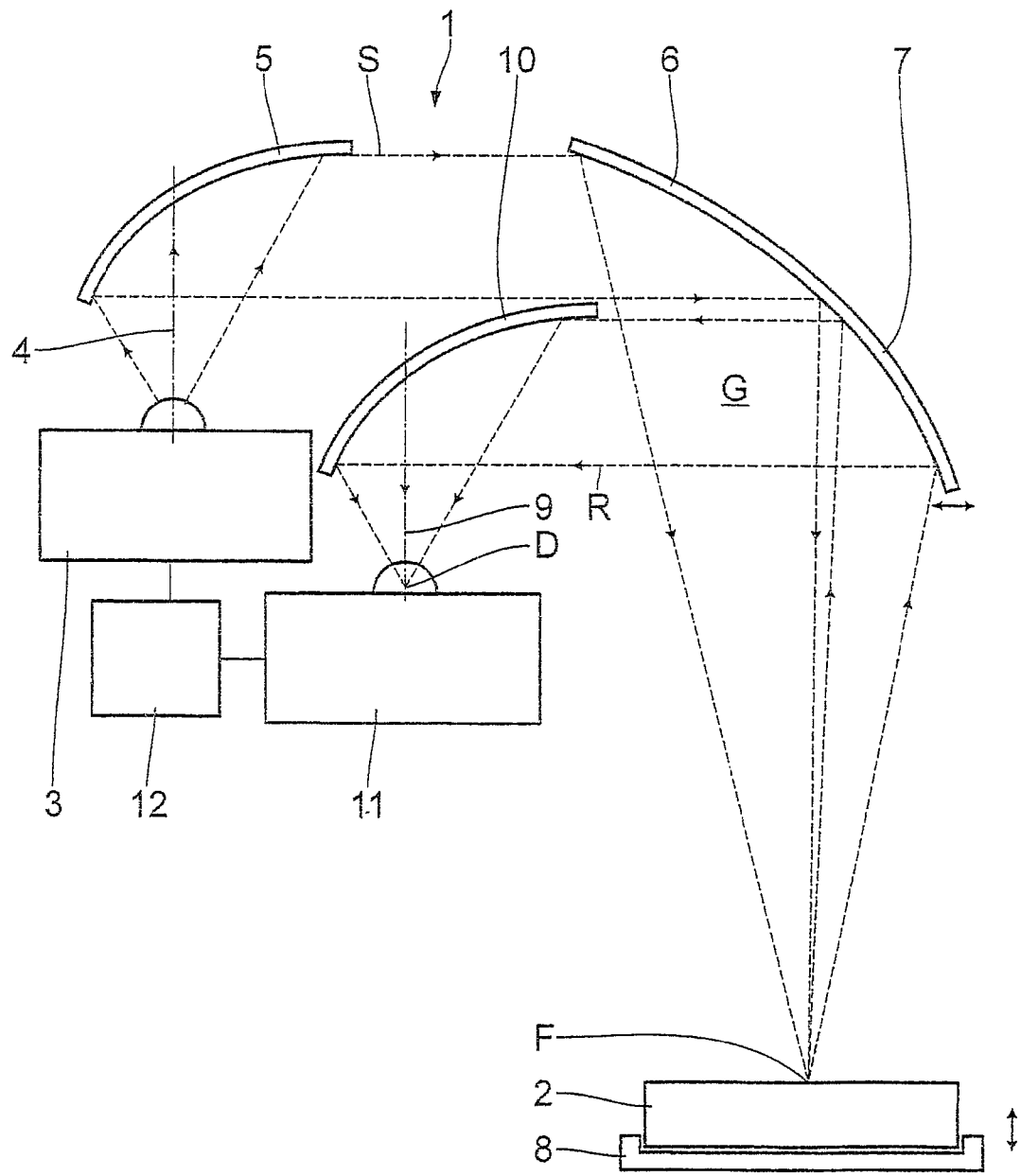
FIG. 5 shows a schematic illustration of a measuring device with mirrors for focusing and aligning the radiation, according to a fifth embodiment.

A fifth embodiment of the invention is described below with reference to FIG. 5. In contrast to the preceding embodiments, the first collimation element 5 and the second focusing element are separately designed as mirrors. The mirrors 5, 10 in particular have a parabolic shape, so that the radiation S emitted in the beam direction 4 is aligned in parallel and deflected transversely, in particular perpendicularly, with respect to the beam direction 4, and the reflected radiation R aligned in parallel is focused and deflected to the receiver 11 in the reflection direction 9. The first focusing element 6 and the second collimation element 7 are designed in one piece as a parabolic mirror, corresponding to the fourth embodiment. In this way, the emitted radiation S is focused and deflected, and the reflected radiation R is collimated and deflected, by means of the first focusing element 6. The measuring device 1 has a compact design. In particular, the test object holder 8 or the test object 2 may be situated downstream from the transmitter 3 and the receiver 11 in the reflection direction 9, since the emitted radiation S and the reflected radiation R are each deflected, in particular by 180°, due to the mirrors 5, 6, 7, and 10. The space between the mirrors 5, 6, 7, and 10 and the test object holder 8 or the test object 2 is filled with a gas G, in particular with air, corresponding to the preceding embodiments. With regard to the further design and the mode of operation of the measuring device 1, reference is made to the preceding embodiments.

The features of the individual embodiments may be combined with one another as needed. In particular, the measuring device 1 may also be operated with electromagnetic waves in other frequency ranges, or with other types of waves, for example ultrasonic waves.

While this invention has been described as having a preferred design, it is understood that it is capable of further modifications, and uses and/or adaptations of the invention and following in general the principle of the invention and including such departures from the present disclosure as come within the known or customary practice in the art to which the invention pertains, and as may be applied to the central features hereinbefore set forth, and fall within the scope of the invention.

What is claimed is:

1. A measuring device for reflection measurements of test objects, comprising:
   a) a transmitter for emitting terahertz radiation;
   b) a first collimation element for aligning the emitted radiation;
   c) a first focusing element for focusing the emitted terahertz radiation relative to a test object;
   d) a receiver for detecting terahertz radiation reflected on a test object;
   e) a second collimation element for aligning the reflected terahertz radiation;
   f) a second focusing element for focusing the reflected terahertz radiation relative to the receiver;
   g) the transmitter and the receiver are offset with respect to one another along a beam direction;
   h) at least two of the first and second collimation elements and the first and second focusing elements are separate from one another;
   i) a control apparatus for controlling the transmitter, and the control apparatus evaluates the reflected and detected terahertz radiation detected by the receiver; and
   j) the control apparatus evaluates the reflected and detected terahertz radiation, and determines a wall thickness of the test object.

2. The measuring device according to claim 1, wherein:
   a) the transmitter and the receiver have an overlap area.

3. The measuring device according to claim 1, wherein:
   a) the first collimation element and the second focusing element are separate from one another.

4. The measuring device according to claim 1, wherein:
   a) one of the first collimation element and the second focusing element is a lens which has a convex design.

5. The measuring device according to claim 1, wherein:
   a) one of the first collimation element and the second focusing element is a mirror which has a parabolic design.

6. The measuring device according to claim 1, wherein:
   a) one of the first collimation element and the second focusing element is separate from the first focusing element and/or the second collimation element.

7. The measuring device according to claim 1, wherein:
   a) the first focusing element and the second collimation element are configured as one single part.

8. The measuring device according to claim 1, wherein:
   a) one of the first focusing element and the second collimation element is a lens which has a convex design.

9. The measuring device according to claim 1, wherein:
   a) one of the first focusing element and the second collimation element is a mirror which has a parabolic design.

10. The measuring device according to claim 1, wherein:
    a) a deflection element for deflecting one of the emitted terahertz radiation and the reflected terahertz radiation is provided.

11. The measuring device to claim 1, wherein:
    a) one of the first focusing element and the second collimation element is displaceable relative to a test object holder and/or relative to the first collimation element and/or the second focusing element.

12. The measuring device according to claim 1, wherein:
    a) a gas is situated at least between two of the first and second collimation elements and the first and second focusing elements.

13. A method for measuring radiation reflected on test objects, including the following steps:
    a) providing a measuring device according to claim 1;
    b) emitting terahertz radiation by use of the transmitter;
    c) aligning the emitted radiation by use of the first collimation element;
    d) focusing the emitted terahertz radiation relative to a test object by use of the first focusing element;
    e) aligning the reflected terahertz radiation by use of the second collimation element;
    f) focusing the reflected terahertz radiation relative to the receiver by use of the second focusing element;
    g) detecting the terahertz radiation reflected on the test object by use of the receiver; and
    h) the reflected and detected terahertz radiation is evaluated, wherein a wall thickness of the test object is determined.

14. The method according to claim 13, wherein:
    a) the reflected and detected terahertz radiation is evaluated, wherein the wall thickness of the test object made of a plastic material is determined.

15. The method according to claim 14, wherein:
    a) a test object made of a plastic material is measured, wherein terahertz radiation is reflected on a front surface and on a rear surface of the test object, and the wall thickness of the test object is determined from the reflected terahertz radiation.

16. The method according to claim 13, wherein:
a) a test object made of a plastic material is measured, by which terahertz radiation is reflected on a front surface and on a rear surface of the test object, and the wall thickness of the test object is determined from the reflected terahertz radiation.

17. The measuring device to claim 1, wherein:
a) a deflection element for deflecting one of the emitted terahertz radiation and the reflected terahertz radiation is provided between the first focusing element and the second collimation element.

18. The measuring device according to claim 1, wherein:
a) the transmitter and the receiver have an overlap area.

19. A measuring device for reflection measurements of test objects, comprising:
a) a transmitter for emitting terahertz radiation;
b) a first collimation element for aligning the emitted radiation;
c) a first focusing element for focusing the emitted terahertz radiation relative to a test object;
d) a receiver for detecting terahertz radiation reflected on a test object;
e) a second collimation element for aligning the reflected terahertz radiation;
f) a second focusing element for focusing the reflected terahertz radiation relative to the receiver;
g) the first collimation element and the second focusing element are offset with respect to one another along a beam direction;
h) at least two of the first and second collimation elements and the first and second focusing elements are separate from one another;
i) a control apparatus for controlling the transmitter, and the control apparatus evaluates the reflected and detected terahertz radiation detected by the receiver; and
j) the control apparatus evaluates the reflected and detected terahertz radiation, and determines a wall thickness of the test object.

20. The measuring device according to claim 19, wherein:
a) the transmitter and the receiver have an overlap area.

* * * * *